US009750469B2

(12) United States Patent
Albanese et al.

(10) Patent No.: US 9,750,469 B2
(45) Date of Patent: Sep. 5, 2017

(54) APPARATUS FOR PERFORMING A BIOPSY ON A PATIENT'S BREAST AND COMPUTER-IMPLEMENTED METHOD FOR DEFINING A ROUTE FOR A BIOPSY NEEDLE THROUGH A PATIENT'S BREAST

(71) Applicant: I.M.S. INTERNAZIONALE MEDICO SCIENTIFICA S.r.l., Sasso Marconi (IT)

(72) Inventors: Achille Albanese, Marzabotto (IT); Bruno Toniolo, Sasso Marconi (IT); Paolo Vignoli, San Giovanni in Persiceto (IT); Sara Vecchio, Casalecchio di Reno (IT)

(73) Assignee: I.M.S. INTERNAZIONALE MEDICO SCIENTIFICA S.R.L., Sasso Marconi (IT)

( * ) Notice: Subject to any disclaimer, the term of this patent is extended or adjusted under 35 U.S.C. 154(b) by 14 days.

(21) Appl. No.: 14/883,271

(22) Filed: Oct. 14, 2015

(65) Prior Publication Data
US 2016/0113599 A1 Apr. 28, 2016

(30) Foreign Application Priority Data
Oct. 24, 2014 (IT) ............................. BO2014A0593

(51) Int. Cl.
*A61B 5/05* (2006.01)
*A61B 6/12* (2006.01)
(Continued)

(52) U.S. Cl.
CPC ............... *A61B 6/12* (2013.01); *A61B 6/025* (2013.01); *A61B 6/0414* (2013.01);
(Continued)

(58) Field of Classification Search
CPC .................................................. A61B 10/0233
See application file for complete search history.

(56) References Cited

U.S. PATENT DOCUMENTS 5,219,351 A * 6/1993 Teubner ................. A61B 6/502
606/130
2010/0191145 A1 7/2010 Lafferty
(Continued)

FOREIGN PATENT DOCUMENTS

| EP | 2491863 A1 | 8/2012 |
| EP | 2526869 A2 | 11/2012 |
| EP | 2656789 A1 | 10/2013 |

OTHER PUBLICATIONS

"Needle Path Planning for Digital Breast Tomosynthesis Biopsy" by L. Vancamberg et al. IEEE Int. Conf. Robotics and Automation. 2010.*
(Continued)

*Primary Examiner* — Tse Chen
*Assistant Examiner* — Jason Ip
(74) *Attorney, Agent, or Firm* — Shuttleworth & Ingersoll, PLC; Timothy J. Klima (57) ABSTRACT

An apparatus for biopsy examination on the breast of a patient, includes: an analysis head including a radiation detection device for detecting X-rays on a detection plane, and a source of X-rays to emit X-rays towards the detector, the source and the detection device being mobile with respect to each other so that they can be placed in a plurality of different working acquisition positions. A biopsy probe can be fixed to a support base includes a needle for extracting a sample of breast tissue and a housing for the needle. The housing is rotatably mounted on the support base to allow modification of the angle of the needle with respect to the breast support surface. A computerized unit is connected
(Continued)

to the detector and configured to produce at least one reconstructed image of a cross-section of the breast.

10 Claims, 10 Drawing Sheets

(51) Int. Cl.
*A61B 10/02* (2006.01)
*A61B 6/02* (2006.01)
*A61B 90/11* (2016.01)
*A61B 6/04* (2006.01)
*A61B 6/00* (2006.01)
*A61B 10/04* (2006.01)

(52) U.S. Cl.
CPC ............ *A61B 6/4452* (2013.01); *A61B 6/469* (2013.01); *A61B 6/502* (2013.01); *A61B 10/0233* (2013.01); *A61B 90/11* (2016.02); *A61B 6/44* (2013.01); *A61B 6/461* (2013.01); *A61B 2010/045* (2013.01)

(56) References Cited

U.S. PATENT DOCUMENTS

| | | |
|---|---|---|
| 2011/0087132 A1 | 4/2011 | DeFreitas et al. |
| 2011/0118625 A1 | 5/2011 | Akuzawa et al. |
| 2012/0302873 A1* | 11/2012 | Tajima .................. A61B 6/025 600/424 |

OTHER PUBLICATIONS

Italian Search Report dated Jun. 15, 2015 for related Italian Application No. IT B020140593.

\* cited by examiner

APPARATUS FOR PERFORMING A BIOPSY ON A PATIENT'S BREAST AND COMPUTER-IMPLEMENTED METHOD FOR DEFINING A ROUTE FOR A BIOPSY NEEDLE THROUGH A PATIENT'S BREAST

This application claims priority to Italian Patent Application No. BO2014A000593 filed Oct. 24, 2014, which application is incorporated by reference herein.

BACKGROUND OF THE INVENTION

This invention relates to an apparatus for performing a biopsy on a patient's breast and to a computer-implemented method for defining a route for a biopsy needle through a patient's breast.

In the technical sector of diagnostic examinations, health care operators strongly feel the need to be able to adjust and/or control the route of the biopsy needle in a particularly quick and easy manner.

The reason is, for example, that doing so allows preventing the needle from passing through certain parts of the breast or allows tissue from desired adjacent areas to be included in the biopsy sample.

In other words, doctors and/or diagnostic examination operators often need to easily adjust and/or control the route followed by the needle through the patient's breast in order to extract a breast tissue sample.

AIM OF THE INVENTION

This invention therefore has for an aim to meet the above mentioned need by providing an apparatus for performing a biopsy on a patient's breast and a computer-implemented method for defining a route for a biopsy needle through a patient's breast.

BRIEF DESCRIPTION OF THE DRAWINGS

The technical features of the invention, with reference to the above aims, are clearly described in the claims below and its advantages are apparent from the detailed description which follows, with reference to the accompanying drawings which illustrate a preferred, non-limiting example embodiment of the invention, and in which:

DESCRIPTION OF THE PREFERRED EMBODIMENTS

With reference to the accompanying drawings, the numeral 100 denotes an apparatus for performing at least one biopsy examination on the breast of a patient.

Figure 1:
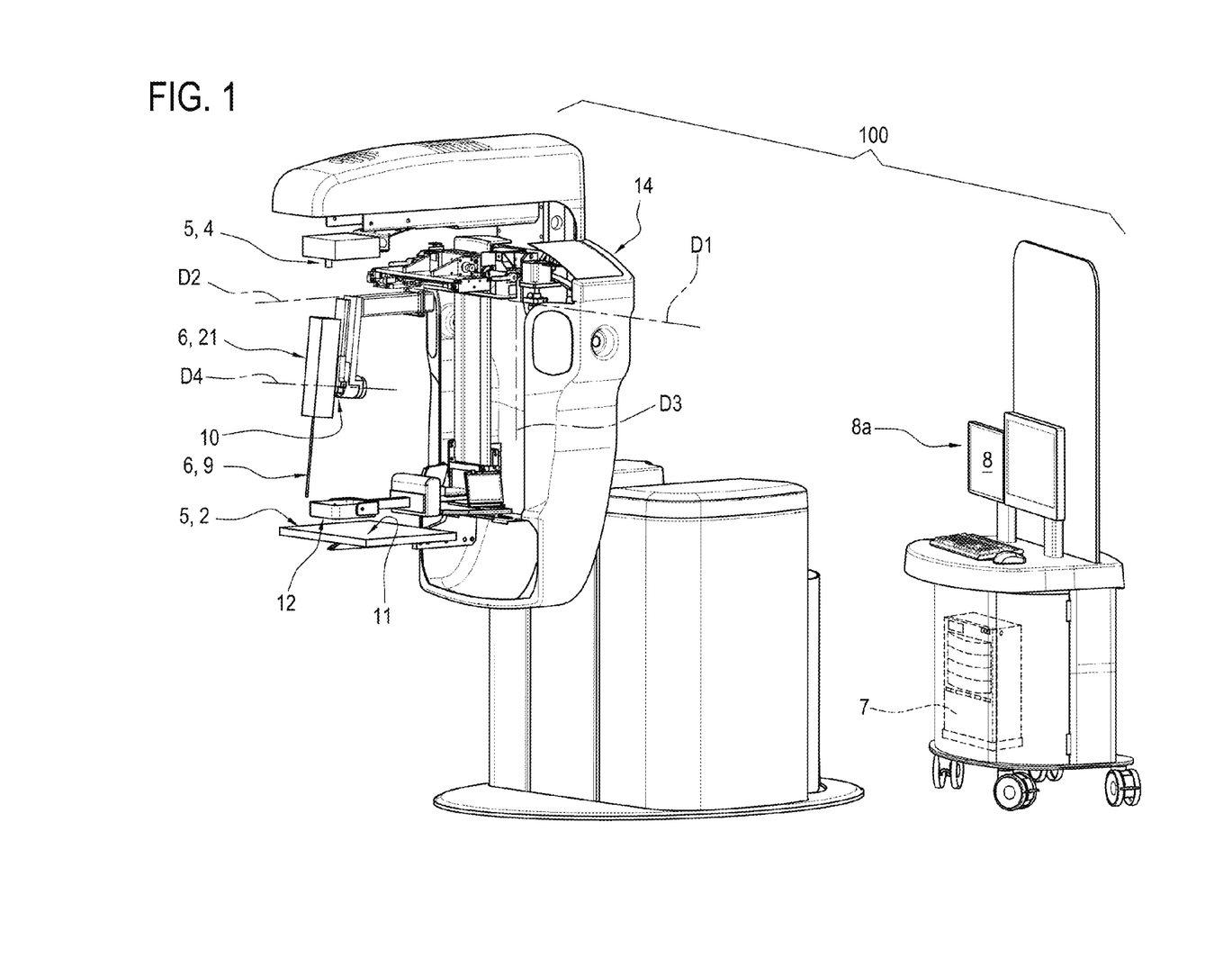
FIG. 1 shows a perspective view of an apparatus according to this invention for performing at least one biopsy examination on a patient's breast.

The apparatus 100 for performing at least one biopsy examination on the breast of a patient comprises:
a frame 14;
a breast support surface 11;
an analysis head 5 provided with at least one radiation detection device 2 configured to detect X-rays and at least one source 4 of X-rays to emit a corresponding beam of X-rays towards the detector 2 on a detection plane, the source 4 and the detection device 2 being mobile with respect to each other so that they can be placed in a plurality of different working acquisition positions;
a support base 10 and a biopsy probe 6 which can be fixed to the support base 10 and which is equipped with a needle 9 for the extraction of a sample of breast tissue and with a housing 21 for the needle 9, this housing 21 being rotatably mounted on the support base 10 to allow modification of the angle of the needle 9 with respect to the breast support surface 11;
a computerized unit 7, connected to the detector 2 and configured to produce at least one reconstructed image I of a cross-section of the breast representative of anatomical portions of the breast at a predetermined depth along a direction at right angles to the detection plane of the detection device 2 based on images of the patient's breast acquired by the detection device 2 in different working positions;
a user interface 8, configured to:
allow the display of the reconstructed image 1 of a cross-section of the breast;
allow selection of a target position P for extraction of the tissue sample;
allow the display of a proposed movement route 9I,9I' of the needle 9 through the patient's breast as far as the target position P for extraction of the tissue sample.

The computerized unit 7 is configured to calculate, based on the selection of the target position P for extraction of the tissue sample, the proposed movement route of the needle through the patient's breast as far as the target position P for extraction of the tissue sample.

Preferably, the support base 10 is movable along three directions: a first direction D1, a second direction D2 and a third direction D3, which are substantially at right angles to each other.

The needle 9 is also mobile with respect to a housing 21 (connectable to the support base 10 either directly or by means of adapters interposed between them) along a longitudinal direction of extension D5.

Figure 2:
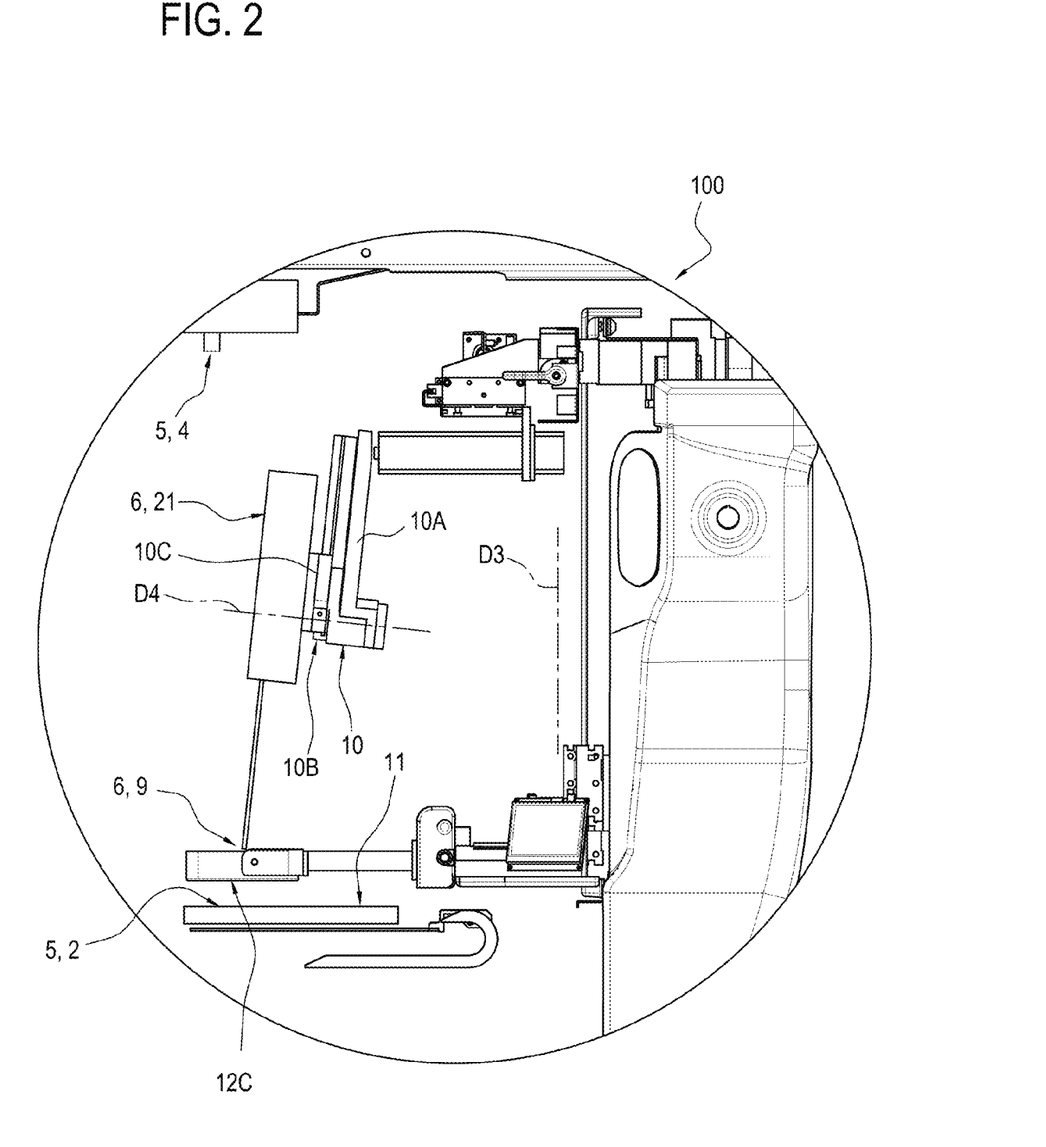
FIGS. 2 to 4 illustrate respective scaled-up details of the apparatus of FIG. 1.
Figure 3:
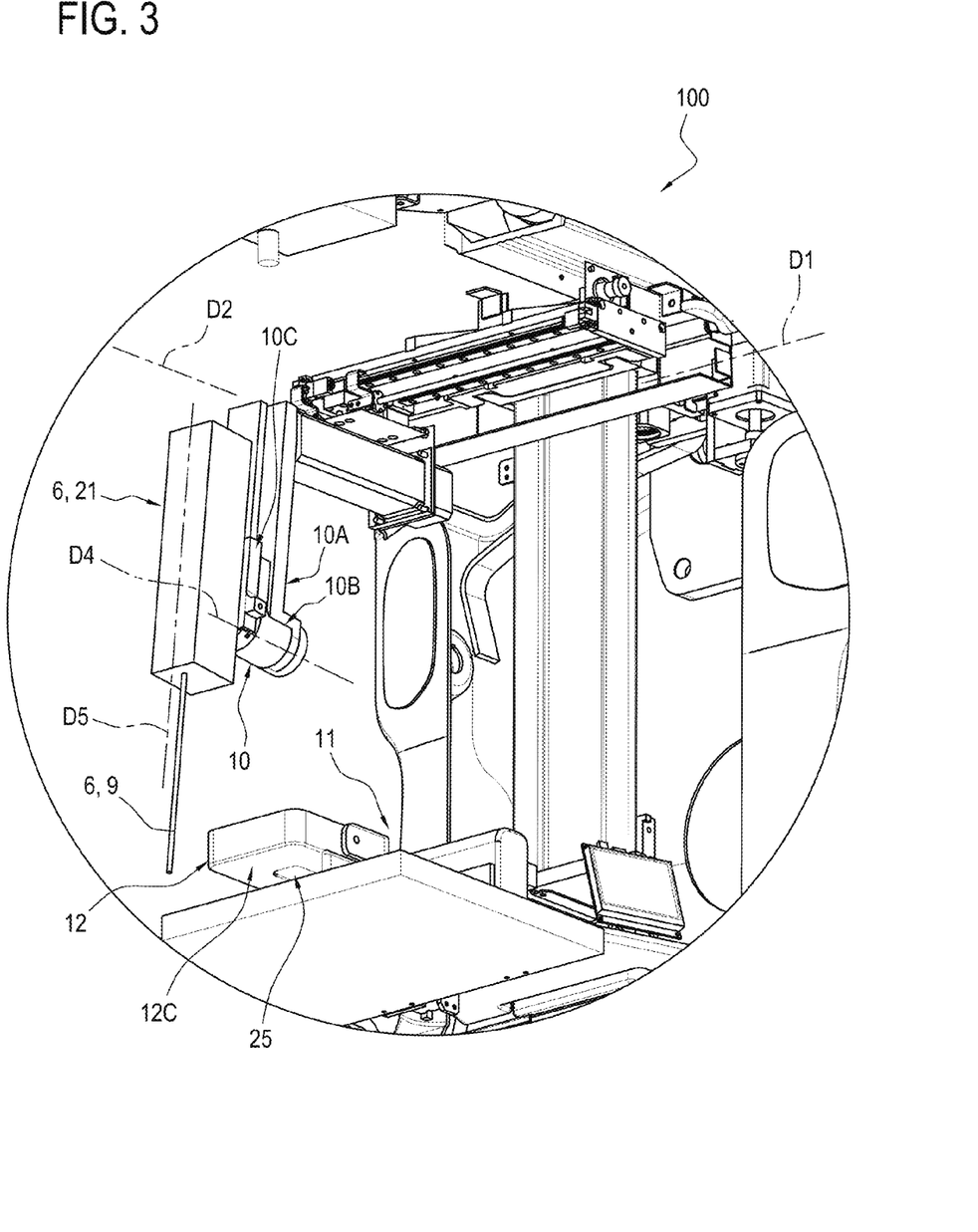
Figure 4:
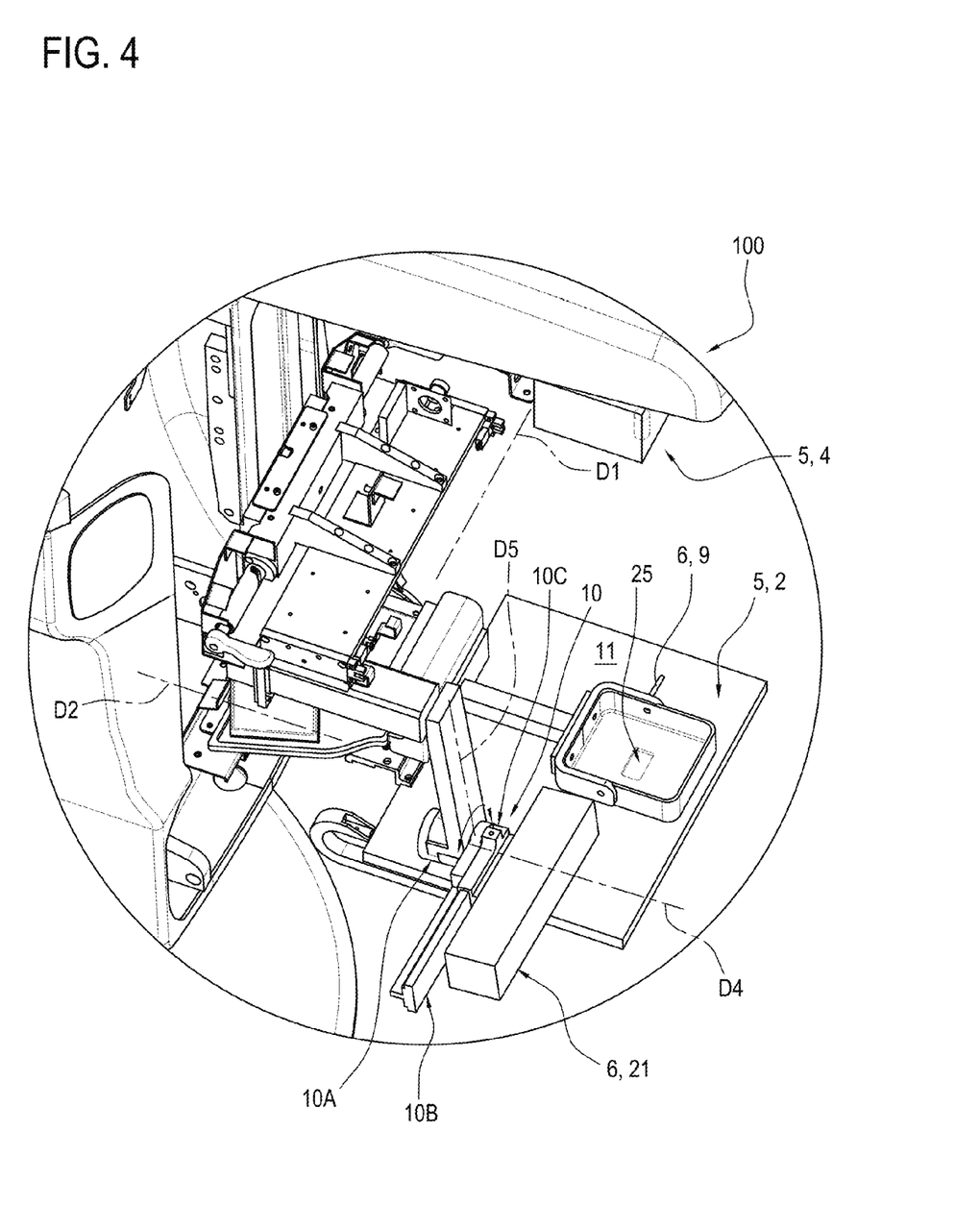

The direction D5 is preferably inclined to the direction of movement D3, that is to say, inclined to a vertical plane (as shown in FIG. 2).

It should also be noted that the housing 21 not only supports, but also acts as a guide for, the needle 9.

The housing 21 also contains the mechanical components for driving ("firing" in the jargon of the sector) the needle 9 along the direction labeled D5.

The housing 21 further comprises means for connecting the suction system by which the tissue sample taken by the needle 9 is extracted.

It should also be noted that the support base 10 comprises two portions, labeled 10A and 10B, which are hinged to each other: the portion 10B is adapted to be connected to the housing 21 (either directly or by means of adapters interposed between them). It should then be noted that the apparatus 1 is equipped with first movement means for moving the support base 10 along the first movement direction D1, second movement means for moving the support base 10 along the second movement direction D2 and third movement means for moving the support base 10 along the third movement direction D3.

It should be noted that in the embodiment illustrated, the housing 21 is connected (directly or indirectly) to a slide 10C which is mobile along the portion 10B (which defines a slide), in particular along the main direction of extension of the portion 10B.

Thus, the portion 10B defines a guide for the slide 10C.

It should be noted that the slide 10C can advantageously be fixed in different longitudinal positions relative to the portion 10B.

In other words, the housing 21 is fixed to the slide 10C which is also coupled to the portion 10B.

More precisely, the slide 10C is mobile parallel to the direction of movement of the needle 9 relative to the housing 21.

The control unit 7 is thus connected to the movement means (first, second, third movement means) which move the base 10 and by which the movement of the support base 10 along one or more directions is controlled.

It should thus be noted that the needle 9, or more specifically, the housing 21 containing it, is rotatably mounted on the base 10 so as to rotate about an axis D4.

Generally speaking, these movement means (first, second or third movement means) comprise an actuator and guide means for guiding the support base 10 along the movement direction (D1; D2; D3).

In practice, therefore, the support base 10, is mobile along three directions (D1, D2, D3) at right angles to each other.

Two of the aforementioned directions of movement (D1, D2) are preferably parallel to the support surface 11.

It should be noted that the housing 21 is rotatable about an axis of rotation D4.

The axis of rotation D4 is preferably inclined to the direction of movement D3, that is to say, inclined to a horizontal plane (as shown in FIG. 2).

According to another aspect, the axis of rotation D4 is preferably at right angles to the direction D5 of movement of the needle 9 relative to the housing 21.

Preferably, the inclination angle of the axis of rotation D4 relative to a horizontal plane is less than 10°.

The apparatus 1 is also equipped with a breast compression element 12 (acting from above the breast support surface 11).

In use, that is, during the biopsy examination, the breast is thus compressed between the compression element 12 and the support surface 11 (positioned above the detection device 2).

The compression element 12 is preferably also provided with an upper opening 25 (or a plurality of such openings) through which the needle 9 can enter the patient's breast from above.

Preferably, the user interface 8 is equipped with a display 8a.

Different aspects of the invention, which may or may not be combined with each other, will now be described.

According to a first aspect, the user interface 8 is configured to allow the selection of the extraction target position P directly on a reconstructed image I of a cross-section of the breast.

Preferably, the interface 8 allows selecting (and displaying) a reconstructed image I of a cross-section of the breast from the plurality of reconstructed cross-sections representing anatomical portions of the breast at different depths along a direction at right angles to the detection plane of the detection device 2 (that is, at right angles to the breast support surface 11 of the detection device 2).

The cross-sectional plane of the images I is substantially parallel to the detection plane of the detection device 2.

It should be noted that, according to this aspect, it is possible to show on the display 8a a selected reconstructed cross-section of the breast, simultaneously displaying its distance from the support surface 11 and from the compression plane 12C (the one facing the breast, defined by the compressor 12).

FIGS. 5 to 9 show respective reconstructed images I of breast cross-sections.

It should be noted that in the drawings, the graphical representation of the compression plane 12C is labeled 12I, the graphical representation of the opening 25 of the compressor 12 is labeled 25I, the graphical representation of the target position is labeled PI and the graphical representation of the breast support surface 11 is labeled 11I.

It should be noted that the reconstructed image I of a cross-section of the breast shown in FIGS. 5 to 9 corresponds substantially to a cross-section of the breast which is centered relative to the line 22I (whose depth is determined by the reconstruction parameters selected). More precisely, FIG. 5 comprises a display of the reconstructed breast cross-section containing the target position.

According to another aspect, the computerized unit 7 comprises a list of biopsy needles 9 and a list of the dimensional and/or geometrical characteristics and/or shapes of the biopsy needles 9.

Figure 6:
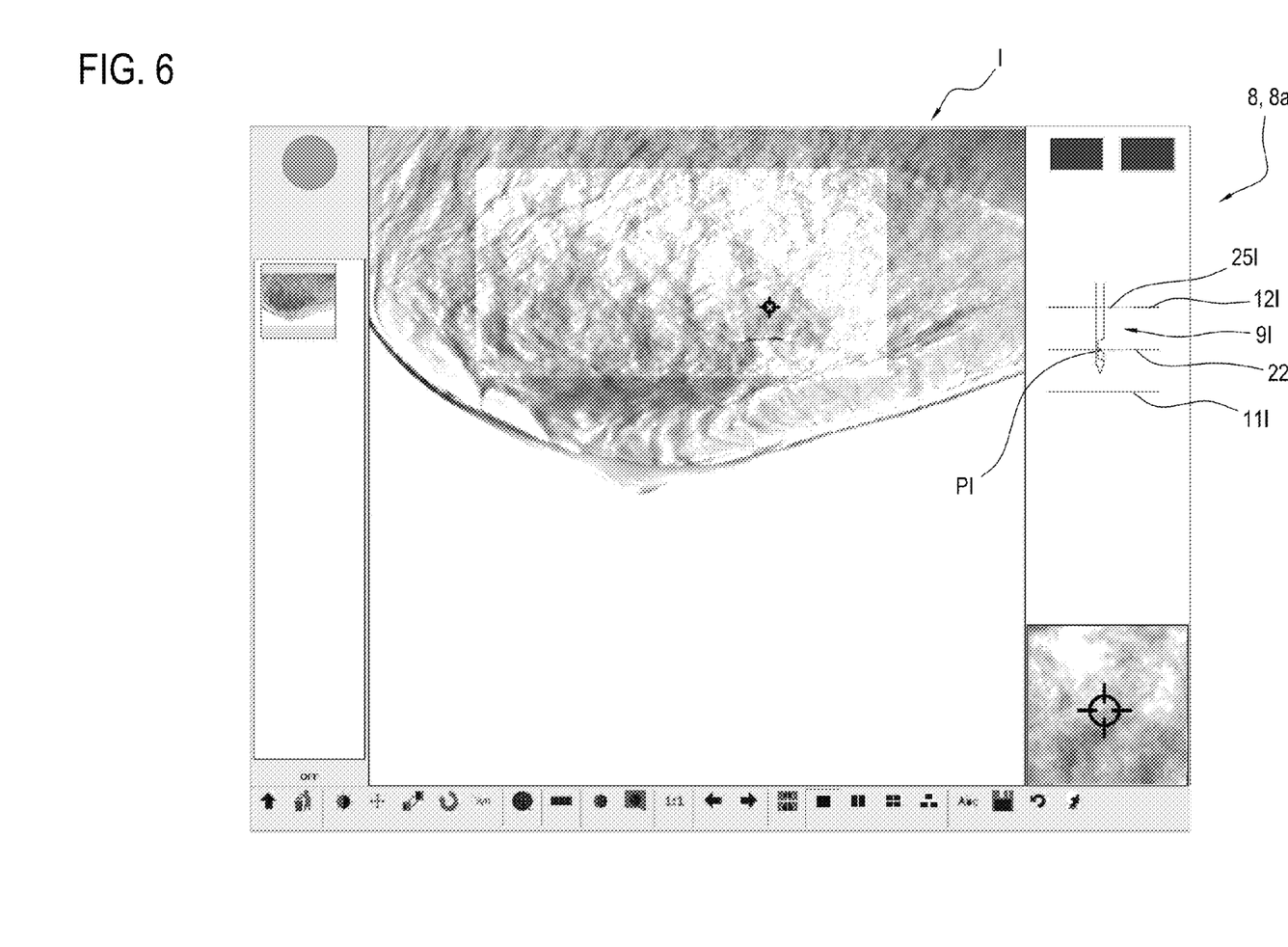

FIG. 6 illustrates the needle approaching vertically (that is, the needle 9 passing through the opening 25 of the compressor) and shows a display of the reconstructed cross-section I of the breast, including the target position.

Figure 7:
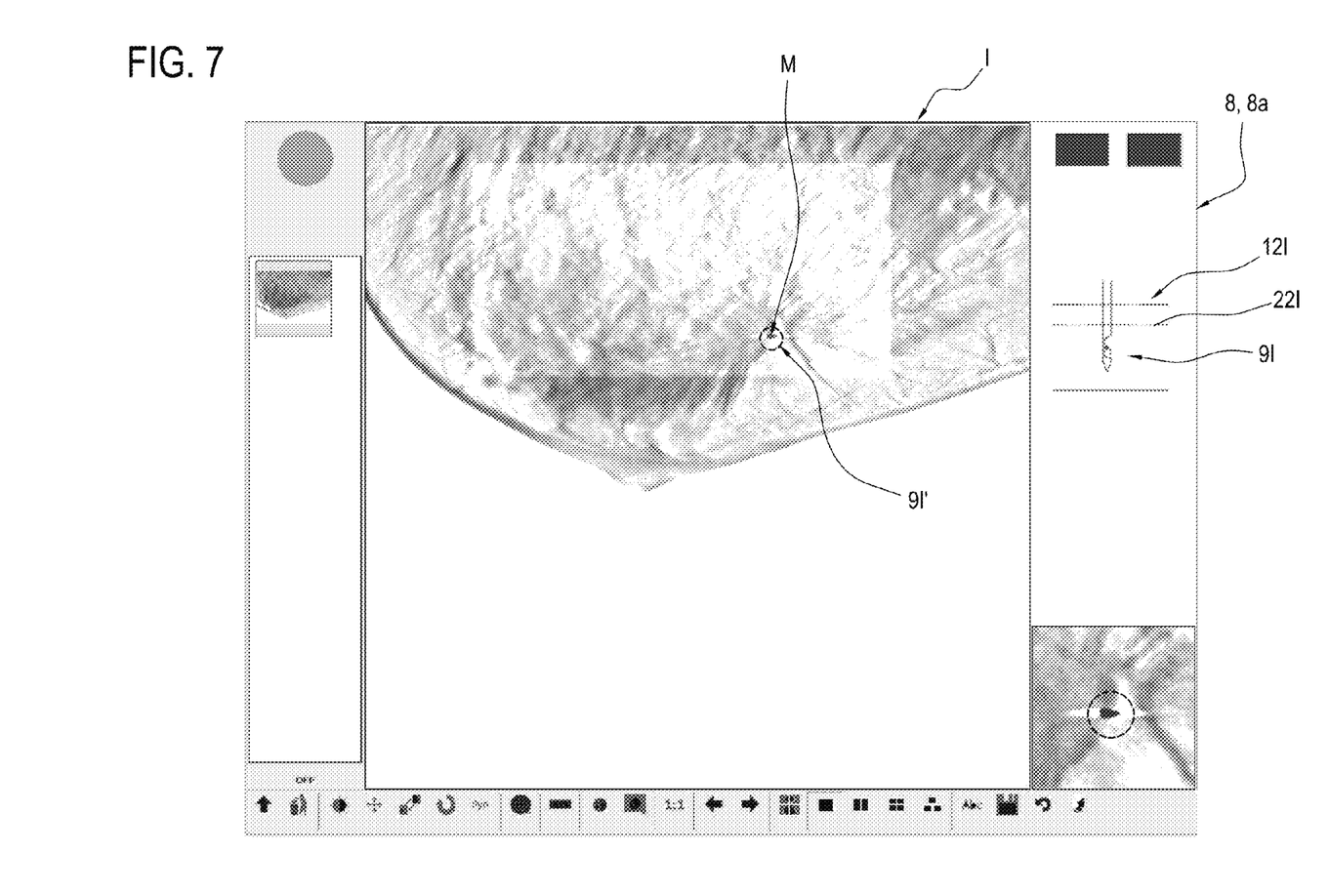
Figure 8:
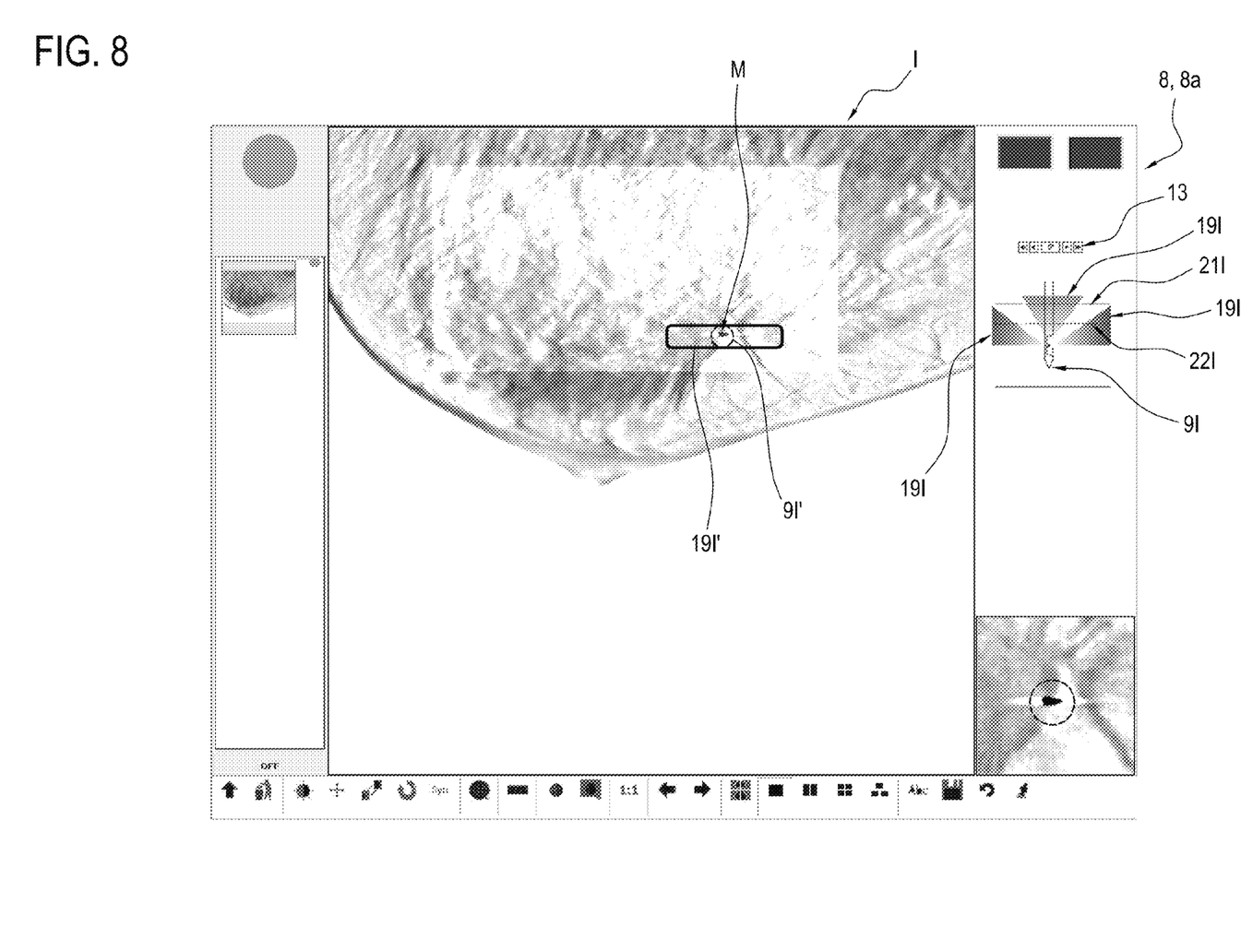
Figure 9:
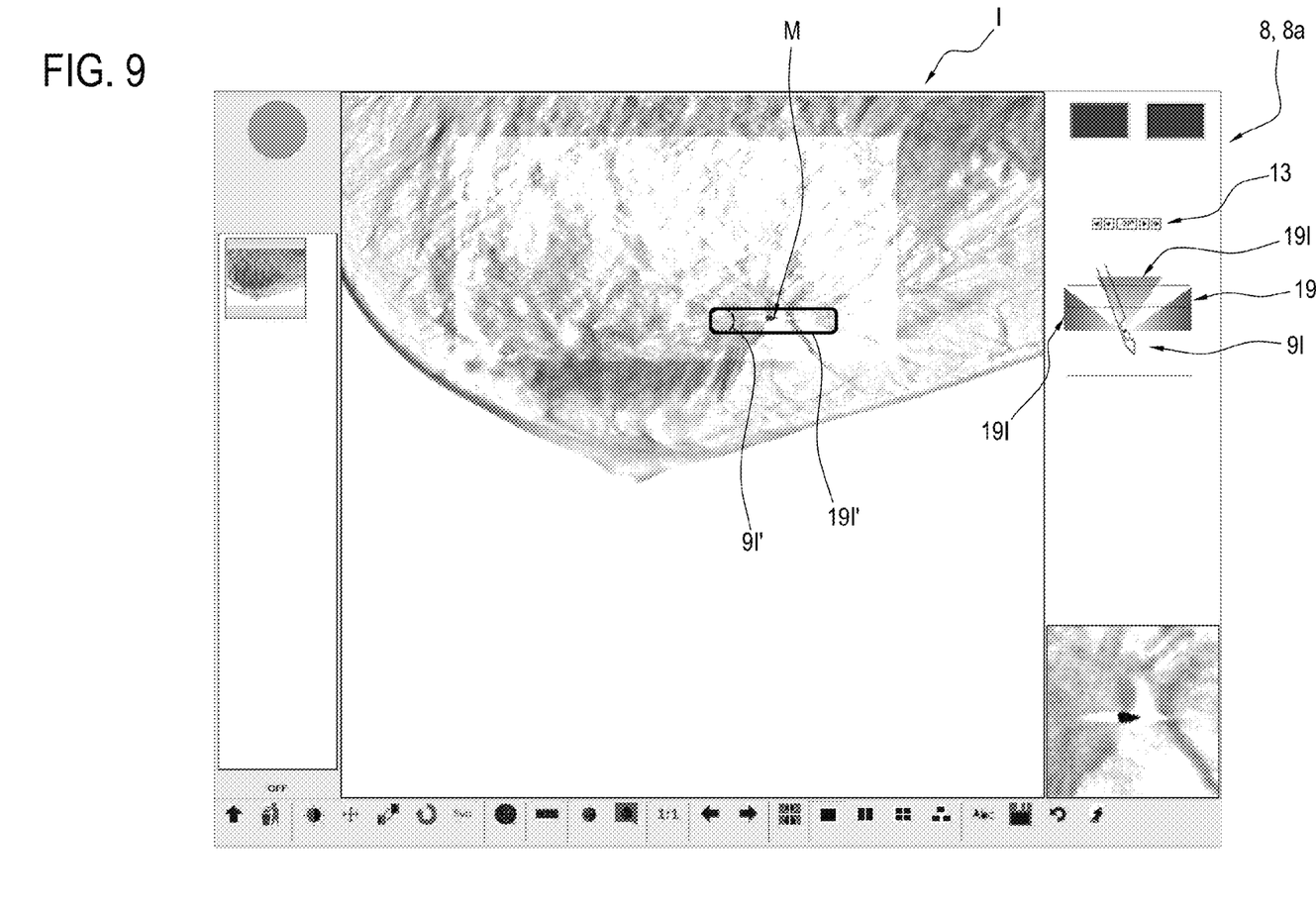

According to another aspect, the interface 8 allows displaying the representation of the crossing route of the selected needle, overlaid on the reconstructed cross-section I of the breast (anatomy). With reference to FIGS. 7 to 9, it should be noted that a graphical representation of the needle 9 overlaid on the reconstructed cross-section I of the breast is labeled 9I'.

FIG. 7 shows a display of a reconstructed cross-section above the one containing the target position, showing a graphical representation 9I' of the crossing route of the needle overlaid on the reconstructed cross-section I of the breast (anatomy).

Preferably, the computerized unit 7 is configured to calculate, for all the needles 9 which can be used, a range of inclinations which allow the needle 9 to reach, and extract the tissue sample from, the target position P without colliding with any parts of the apparatus (that is to say, safely).

In other words, the computerized unit 7 calculates all the ranges of inclination (inclination angles) by which it is possible to reach the target position P (considering all the needles in the list and not just one).

According to this aspect, the user interface 8 is preferably configured to display an image 9I of a needle 9 and a graphic indicator 19I representing the range of possible inclinations, for all the needles 9 which can be used, which allow the target position P to be reached without colliding with any parts of the apparatus (that is to say, safely).

With reference to FIGS. 8 and 9, it should be noted that a graphical representation of all the possible angles of the needle overlaid on the reconstructed cross-section I of the breast is labeled 19I'.

FIG. 8 comprises a representation of the needle 9 approaching vertically and a display of a reconstructed cross-section I of the breast overlaid on the one containing the target position.

FIG. 8 also comprises a representation 9I' of the needle crossing route (or needle crossing zone) overlaid on the reconstructed image representing the breast (anatomy) and a display of all the possible angular approaches, including a graphical representation of these angular approaches 19I' overlaid on the reconstructed image I of the breast (anatomy).

It should be noted that the graphical indicator 19I representing the range of possible inclination angles preferably comprises one or more triangles whose sides define the possible limit inclinations (inclination angles) of the needle.

It should be noted that the indicator 19I' of the range of possible crossing routes (or of the possible inclination angles) of the needle on the reconstructed cross-section I of the breast preferably comprises only the inclination ranges during approach from above, that is, those where the crossing route of the needle 9 passes through the opening 25 of the compressor.

Considering FIGS. 8 and 9, for example, it is evident that the graphical indicator 19I comprises three triangles (representing three ranges of possible inclination angles of the needle), a left-hand triangle (representing the inclination angles of the needle approaching and entering the breast from the left), a middle triangle (representing the inclination angles of the needle approaching from above, that is through the window or opening 25 of the compressor 12) and a right-hand triangle (representing the inclination angles of the needle approaching and entering the breast from the right).

According to another aspect, the computerized unit 7 comprises a list of biopsy needles 9 and the dimensional and/or geometrical characteristics and/or shapes of these biopsy needles 9 and the user interface 8 is configured to allow the selection of a needle 9 from the list of needles 9.

Advantageously, therefore, the interface allows the user to select the needle 9 most suitable for the tissue sample to be extracted.

According to another aspect, the proposed movement route of the needle through the patient's breast as far as the target position P for extraction of the tissue sample corresponds to the shortest route from the exterior of the breast to the target position P.

In other words, according to this aspect, the computerized unit 7 is configured to calculate the shortest route from the exterior of the breast to the target position P (compatibly with the overall safety of the system, that is, avoiding collisions and proposing routes which actually reach the target position P).

An example of this aspect is illustrated in FIGS. 6 and 7.

It should be noted that this, in most cases, corresponds to the vertical approach, that is to say, the one which, to date, is most commonly used, and hence the quickest.

The apparatus proposed makes it possible to not increase the complexity of the examination unless actually necessary.

That means the user is provided with a particularly quick method to generate a possible route to reach the target position P.

According to another aspect, the user interface 8 is configured to allow selecting an obligatory crossing position of the biopsy needle 9 in the reconstructed image I of a cross-section of the breast and the computerized unit 7 is configured to calculate, based on the selection of the target position P for extraction of the tissue sample and on the selected obligatory crossing position of the needle 9, an angle of the needle 9 and the movement route to reach the target position P passing through the obligatory position.

This approach allows making the needle pass through a desired position (obligatory crossing position of the needle) and generating in a particularly rapid and computationally light manner a route to the target position which includes passing through the selected position (obligatory crossing position of the needle).

Advantageously, therefore, by suitably selecting the obligatory crossing position of the needle, it is possible to exclude routes which cross certain areas (for example, areas where a tissue sample has already been extracted, identifiable by means of suitable markers M left inside the breast by operators who performed the previous examination).

In this regard, FIG. 9 illustrates an oblique approach of the needle 9 to exclude the route which crosses an area inside the breast where a marker M has been placed.

The user interface 8 is also provided with controls (physical and/or touch-screen and/or vocal) which allow selection of the obligatory crossing position of the needle 9.

Preferably, selection occurs directly on the graphical representation of the needle 9, for example on the representation 9I or 9I'.

Further, by selecting an obligatory area which the needle must cross, it is possible to optimally control extraction of the tissue sample: in effect, it must be considered that since the needle 9 presents a certain window size (longitudinally), it is possible, by selecting two crossing points (target position and obligatory crossing position) to extract an extended sample which includes both an area proximal to the target position and an area proximal to the obligatory position.

According to another aspect, the user interface 8 is configured to allow the selection of a predetermined angle of the needle 9 and the computerized unit 7 is configured to calculate a route of the needle 9 towards the target position P such that the selected angle of the needle 9 is maintained.

Advantageously, according to this aspect, the user can, by means of the interface 8, select the inclination angle of the needle 9 (from among the possible inclination angles calculated by the control unit 7 for the needles 9 of the list or for the selected needle).

Thus, the interface 8 is provided with pushbuttons or controls which allow the user to select the inclination angle of the needle 9.

Some of the accompanying drawings are briefly described below.

Figure 10:
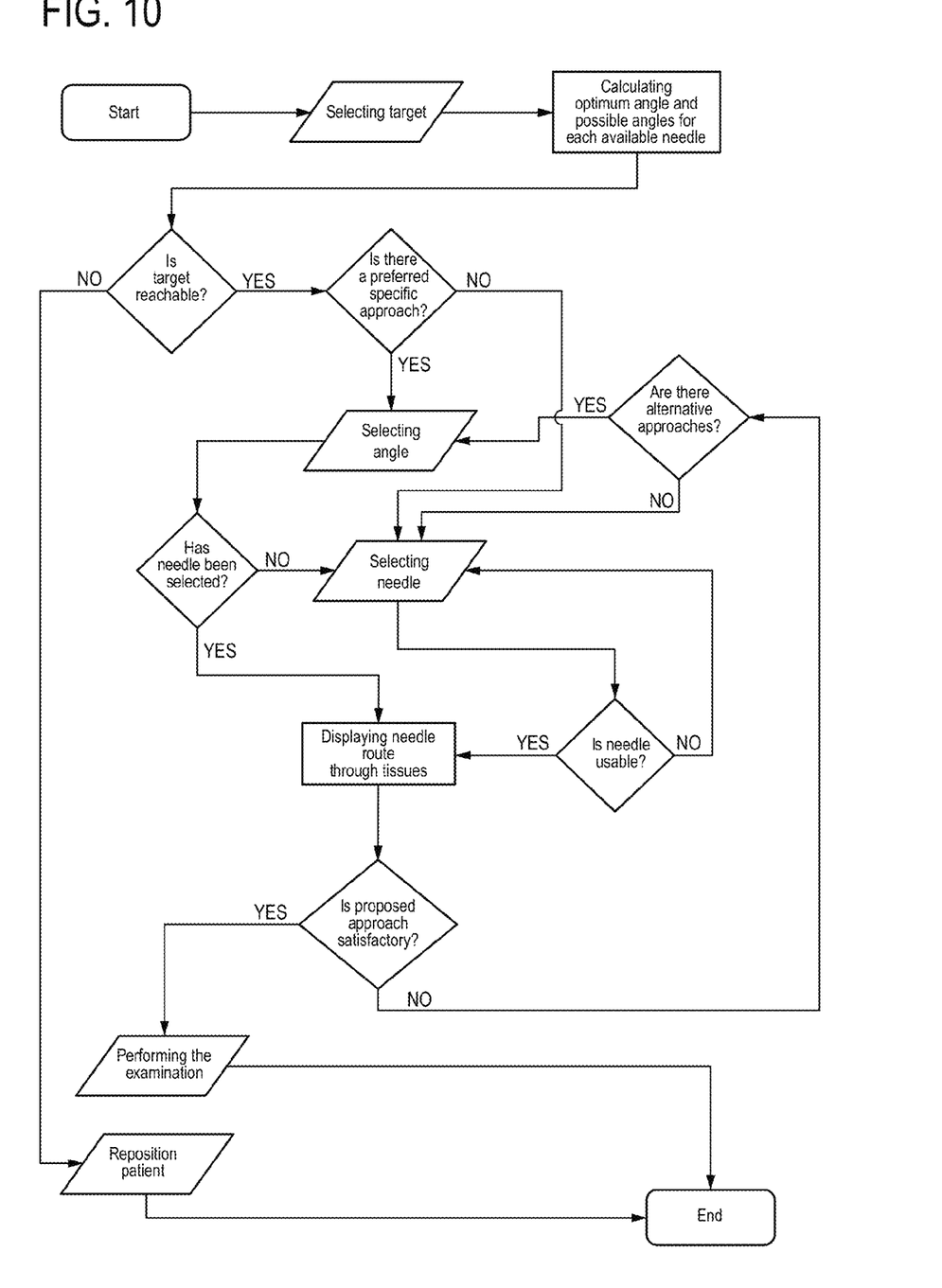
FIG. 10 schematically represents the steps of the method of this invention according to a preferred embodiment of it.

FIG. 10 shows a flow-chart of a possible operating mode of the apparatus 1.

Figure 5:
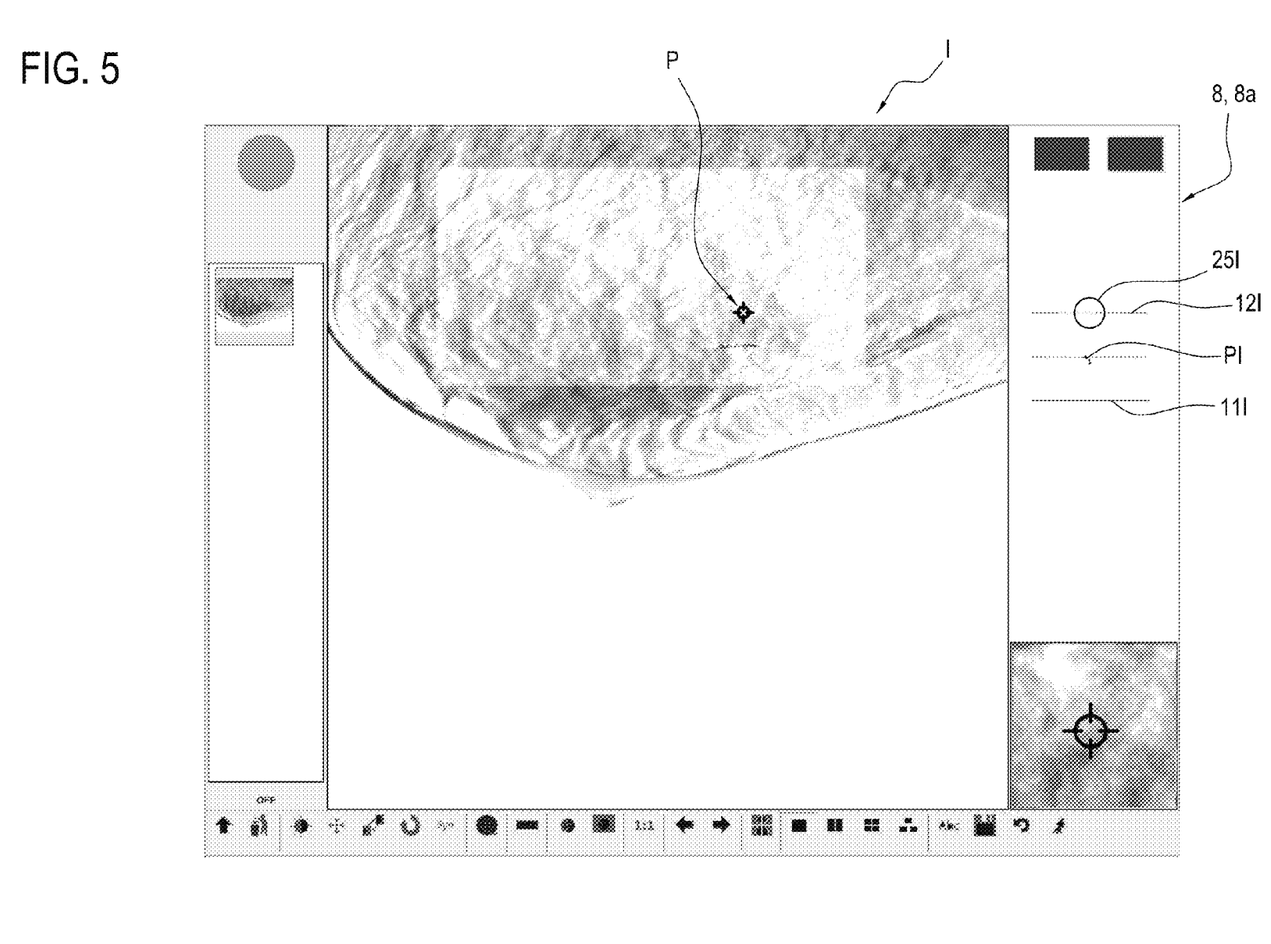
FIGS. 5 to 9 show respective schematic views of displays provided by the display 8a of the apparatus of the preceding figures.

FIG. 5 in particular relates to the step labeled "Selecting target" in FIG. 10.

FIG. 6 in particular relates to the step labeled "Selecting needle" in FIG. 10.

FIG. 7 in particular relates to the step labeled "Displaying needle route through tissues" in FIG. 10.

FIGS. 8 and 9, on the other hand, relate to the step labeled "Selecting angle" in FIG. 10.

FIGS. 8 and 9 also show a representation 9I' of the crossing route of the needle 9 overlaid on the reconstructed image I of the breast (anatomy).

FIGS. 8 and 9 also comprise a display of all the possible angular approaches by means of a representation 19I' overlaid on the reconstructed image of the breast (anatomy).

Also defined according to the invention is a computer-implemented method for defining a route of a biopsy needle 9 through the breast of a patient, comprising the following steps:

providing an apparatus 100 as described in the foregoing;

displaying, on the user interface 8, a reconstructed image I of a cross-section of the breast representative of anatomical portions of the breast at a predetermined depth along a direction at right angles to the detection plane of the detection device 2;

selecting, by means of the user interface 8, a target position P to be reached;

calculating, by means of the computerized unit 7, at least one route for the needle 9 to reach the target position P;

allowing the display 9I, 9I' of the route of the needle 9 in the reconstructed image I of a cross-section of the breast.

It should be noted that the method advantageously makes it possible to modify the needle route particularly easily in order to adapt it to the requirements of the examination being performed.

What is claimed is:

1. An apparatus for carrying out a biopsy examination on a breast of a patient, comprising:
   an analysis head including a radiation detection device configured to detect X-rays on a detection plane and acquire images of the breast, and a source of X-rays to emit a corresponding beam of X-rays towards the detector, the source and the detection device being mobile with respect to each other so that they can be placed in a plurality of different working acquisition positions;
   a breast support surface;
   a support base and a biopsy probe attached to the support base and which includes a selected biopsy needle for extraction of a tissue sample from the breast and a housing for the selected biopsy needle, the housing being rotatably mounted on the support base to allow modification of an angle of the selected biopsy needle with respect to the breast support surface;
   a control unit comprising a computer operatively connected to the detector for receiving the images of the breast and configured to produce a reconstructed image of a cross-section of the breast representative of anatomical portions of the breast at a predetermined depth along a direction at right angles to the detection plane of the detection device based on the images of the breast acquired by the detection device in different working positions;
   a user interface operatively connected to the control unit, configured to:
      allow display of the reconstructed image of the cross-section of the breast;
      allow selection of a target position for extraction of the tissue sample;
      allow display of a proposed movement route of the selected biopsy needle through the breast as far as the target position for extraction of the tissue sample;
   the control unit being configured to calculate, based on the selection of the target position for extraction of the tissue sample, the proposed movement route of the selected biopsy needle through the breast as far as the target position for extraction of the tissue sample and wherein the user interface is configured to allow the display of the proposed movement route of the selected biopsy needle through the breast, as far as the target position for extraction of the tissue sample, directly on the reconstructed image of the cross-section of the breast;
   wherein the control unit comprises a list of biopsy needles and at least one chosen from dimensional characteristics, geometrical characteristics and shapes of the biopsy needles, the control unit being configured to calculate a range of angles for all the biopsy needles that can be used to reach the target position and extract the tissue sample without collisions;
   wherein the user interface is configured to display a biopsy needle image and a graphic indicator representative of the range of angles, for all the biopsy needles that can be used to reach the target position;
   wherein the user interface is configured to allow selection of the selected biopsy needle from the list of biopsy needles.

2. The apparatus according to claim 1, wherein the user interface is configured to allow the selection of the target position directly on the reconstructed image of the cross-section of the breast.

3. The apparatus according to claim 1, wherein the user interface is configured to allow the selection of an obligatory crossing position of the selected biopsy needle in the reconstructed image of the cross-section of the breast and wherein the control unit is configured to calculate, based on the selection of the target position for extraction of the tissue sample and on the obligatory crossing position of the selected biopsy needle, an angle of the selected biopsy needle and the movement route to reach the target position passing through the obligatory position.

4. The apparatus according to claim 1, wherein the user interface is configured to allow the selection of a predetermined angle of the selected biopsy needle and the control unit is configured to calculate a route of the selected biopsy needle towards the target position wherein the selected angle of the selected biopsy needle is maintained.

5. The apparatus according to claim 1, wherein the proposed movement route of the selected biopsy needle through the breast as far as the target position for extraction of the tissue sample corresponds to a shortest route from an exterior of the breast to the target position.

6. The apparatus according to claim 1, wherein the user interface is configured to allow display of the reconstructed image of the cross-section of the breast selected from a plurality of reconstructed images of cross-sections of the breast representative of anatomical portions of the breast at different depths along the direction at right angles to the detection plane of the detection device.

7. The apparatus according to claim 1, wherein the support base is mobile along a first direction, a second direction and a third direction arranged at angles to each other.

8. The apparatus according to claim 1, wherein the support base comprises at least two portions hinged to each other, one of these portions being connected directly or indirectly to the housing so that the housing can be rotated with respect to the other portion.

9. A computer-implemented method for defining a route of a biopsy needle through a breast of a patient, comprising:
   providing an apparatus comprising:
      an analysis head including a radiation detection device configured to detect X-rays on a detection plane and acquire images of the breast, and a source of X-rays to emit a corresponding beam of X-rays towards the detector, the source and the detection device being mobile with respect to each other so that they can be placed in a plurality of different working acquisition positions;
      a breast support surface;
      a support base and a biopsy probe attached to the support base and which includes a selected biopsy needle for extraction of a tissue sample from the breast and a housing for the selected biopsy needle, the housing being rotatably mounted on the support base to allow modification of an angle of the selected biopsy needle with respect to the breast support surface;
      a control unit comprising a computer operatively connected to the detector for receiving the images of the breast and configured to produce a reconstructed image of a cross-section of the breast representative of anatomical portions of the breast at a predetermined depth along a direction at right angles to the detection plane of the detection device based on the images of the breast acquired by the detection device in different working positions;

a user interface operatively connected to the control unit, configured to:
  allow display of the reconstructed image of the cross-section of the breast;
  allow selection of a target position for extraction of the tissue sample;
  allow display of a proposed movement route of the selected biopsy needle through the breast as far as the target position for extraction of the tissue sample;

the control unit being configured to calculate, based on the selection of the target position for extraction of the tissue sample, the proposed movement route of the selected biopsy needle through the breast as far as the target position for extraction of the tissue sample and wherein the user interface is configured to allow the display of the proposed movement route of the selected biopsy needle through the breast, as far as the target position for extraction of the tissue sample, directly on the reconstructed image of the cross-section of the breast;

wherein the control unit comprises a list of biopsy needles and at least one chosen from dimensional characteristics, geometrical characteristics and shapes of the biopsy needles, the control unit being configured to calculate a range of angles for all the biopsy needles that can be used to reach the target position and extract the tissue sample without collisions;

wherein the user interface is configured to display a biopsy needle image and a graphic indicator representative of the range of angles, for all the biopsy needles that can be used to reach the target position;

wherein the user interface is configured to allow selection of the selected biopsy needle from the list of biopsy needles;

displaying, on the user interface, the reconstructed image of the cross-section of the breast representative of anatomical portions of the breast at a predetermined depth along the direction at right angles to the detection plane of the detection device;

selecting, via the user interface, the target position to be reached;

calculating, with the control unit, the proposed movement route for the biopsy needle to reach the target position;

displaying the proposed movement route of the biopsy needle on the reconstructed image of the cross-section of the breast.

10. The apparatus according to claim 1, wherein the user interface is configured to allow the display of a graphical image of the selected biopsy needle overlaid on the reconstructed image of the cross-section of the breast.

\* \* \* \* \*